United States Patent [19]

Chamberlin, Sr.

[11] Patent Number: Plant 6,153

[45] Date of Patent: Apr. 19, 1988

[54] PLUM TREE, "EBONY SUN"

[75] Inventor: Thomas O. Chamberlin, Sr., Visalia, Calif.

[73] Assignees: Metzler Investments; Metropolitan Life Insurance Company, both of Del Ray, Calif.

[21] Appl. No.: 853,136

[22] Filed: Apr. 17, 1986

[51] Int. Cl.[4] ..... A01H 5/03

[52] U.S. Cl. ..... Plt./38

[58] Field of Search ..... Plt./38

*Primary Examiner*—Robert E. Bagwill
*Attorney, Agent, or Firm*—Worrell & Worrell

[57] ABSTRACT

A plum tree broadly characterized by producing fruit which has a Black skin color and firm, Deep Orange Yellow colored flesh and whose harvesting date is September 6 through September 10 at Del Rey, Calif.

1 Drawing Sheet

BACKGROUND OF THE NEW VARIETY

The present invention relates to a new and distinct variety of plum tree which has been denominated by the varietal name, "Ebony Sun", and which is characterized as to novelty by producing a large, black plum having a deep yellow flesh, a mild taste and which is mature for harvesting at approximately September 6 through September 10 at Del Rey, Calif. The flesh of the subject plum has a quite juicy characteristic and has a bloom date of approximately one week later than the Santa Rosa Plum Tree (unpatented), or approximately March 8, at Del Rey, Calif.

For decades, the applicant has endeavored to produce new and novel varieties of fruit trees for his employer, H. P. Metzler & Sons Company of Del Rey, Calif. In this regard, the applicant is perpetually on the alert for newly found seedlings and sports among his employer's various orchards as he proceeds about discharging his various responsibilities. As a part of his regular duties, the inventor has regularly procured mixtures of various types of seeds from his employer's Ranch No. 5, which is located near Del Rey, Calif., germinated the subject seeds and thereafter evaluated the subject seedlings to determine if any new, useful and novel varieties are present. "Ebony Sun" was a newly found seedling discovered using the foregoing procedure. In the fall of 1979, a mixed lot of seeds was procured from the applicant's employer's Ranch No. 5 and was thereafter planted in the H. P. Metzler & Sons nursery, in the spring of 1980. The new seedlings bore their first fruit in 1982. At that time, "Ebony Sun" was first identified as having unique characteristics in that the date of harvest was noted to be early in September. This was somewhat unique in light of the knowledge of the applicant that the mixed seedlot which had been procured from Ranch No. 5 came from parent trees that had the settled characteristic of producing fruit mature for harvest in the month of July.

ASEXUAL REPRODUCTION OF THE NEW VARIETY

The seedling, of unknown origin, was noted for producing fruit of the characteristics and quality which the applicant's employer was seeking. As a consequence, budwood was collected from the parent trees, in the winter of 1982, and was thereafter budded to seedling test trees in the H. P. Metzler & Sons test block in the nursery located at Del Rey, Calif. These budded test trees produced their first fruit in 1984 and again in 1985. The budded plum trees have been continuously observed by the applicant and have proved to be identical in characteristics to those displayed by the original seedling to which reference has been made.

SUMMARY OF THE NEW VARIETY

The instant variety of plum tree is characterized as to novelty by producing a fruit which ripens late in the season, approximately September 6 through September 10. The fruit has a black-colored skin with a deep orange-yellow flesh, which has a mild flavor, is nearly freestone by nature, and displays excellent storage qualities.

BRIEF DESCRIPTION OF THE DRAWING

The accompanying drawing is a color photograph of a characteristic twig bearing typical leaves, several plums in various attitudes displaying their external coloration sufficiently mature for harvesting and shipment, and a plum halved transversely of the suture plane to illustrate the flesh coloration, and stone characteristics.

DETAILED DESCRIPTION

Referring more particularly to the pomological details of this new and distinct variety of plum tree, the following has been observed under the ecological conditions prevailing in the designated orchards near Del Rey, Calif. All color code identifications are made by reference to the Inter-Society Color Council, National Bureau of Standards. Common descriptive color names are also used occasionally.

TREE

Size: Normal.

Vigor: Vigorous.

Figure: Upright growth and as modified by pruning.

Productivity: Good, productivity is dependent upon the presence of other plum tree varieties which aid in the pollination of the new variety.

Regularity of bearing: Good; fruition is dependent upon the presence of other plum tree varieties which will aid in the pollination of the new variety.

Trunk:

*Diameter in relation to length.*—Normal.

*Bark texture.*—Rough; the plum bark is average in appearance.

*Lenticels.*—Approximately 25 to 28 per square inch.

*Lenticel size.*— Medium; approximately ¼ inch in length, (6.35 mm.).

*Lenticel color.*—(75 deep y. Br.).

*Color of bark.*—Brown with some Black (162 d. gy. Br.), and (65 br. black).

Branches:

*Size.*—Average.

*Surface texture.*—Same as the trunk.

*Color.*—(62 d. gy. Br).

*Lenticels — number.*—Approximately 25 to 28 per square inch.

*Lenticels — size.*—Medium, approximately ¼ inch in length (6.35 mm.).

*Lenticels — color.*—(75 deep y. Br.).

LEAVES

Size: Average.

*Length.*—Approximately 2¼ inches to 3¼ inches, (57.15 through 82.55 mm.).

*Width.*—Approximately 1¼ 1 inches to 1⅝ inches (31.75 through 41.275 mm.).

*Shape.*—Lanceolate.

*Color — dorsal surface.*—(127 gy. 01. G.).

*Color — ventral surface.*—(122 g.y. G.).

*Marginal form.*—Doubly serrate.

*Shape of glands.*—Globose.

*Petiole.*—Length — approximately 9/16 inch, (14.288 mm.). Thickness — approximately 1/16 inch, (1.588 mm.).

*Stem glands.*—Number — one pair. Arrangement — opposite to each other. Color — (122 g.y. y.G.). Size — approximately 1/32 inch, (0.794 mm.).

*Stipules.*—None evident.

Flower buds:

*Size.*—Length — approximately 3/16 inch (4.762 mm.). Diameter — approximately ⅛ inch (3.175 mm.): The measurement determined at a time where white coloration is appearing at the apex.

*Shape.*—Slightly elongated.

*Petiole.*—Length — approximately ⅛ inch (3.175 mm.).

*Color.*—Light Green (119 L. Y. G.).

*Other characteristics — Bud development occurs separately on spurs.*

Flowers:

*Date of bloom.*—Approximately February 20 through February 25 at Del Rey, Calif. or approximately eight days after ripening of fruit of the Santa Rosa Plum Tree.

*Size of Petal.*—Length — approximately 5/16 inch (7.938 mm.); Diameter — approximately ¼ inch, (6.350 mm.).

*Shape.*—Slightly elongated, however it appears to be generally roundish.

*Color.*—White (263 White).

*Petiole.*—Length — approximately 5/16 inch (7.938 mm.) at full bloom.

FRUIT

Maturity when described: Mature for harvesting approximately September 6 through September 10 at Del Rey, Calif.

Size:

*Uniformity.*—Uniform.

*Axial diameter.*—Approximately 2¼ inches to 2½ inches (57.15 through 63.5 mm.).

*Diameter transverse in the suture plane.*—Approximately 2½ inches, (63.5 mm).

*Diameter transverse in the cheek plane.*—Approximately 2½ inches (63.5 mm.).

Form:

*Uniformity.*—Noteworthy.

*Shape.*—Nearly round; occasionally, however, some fruit may be found that are somewhat elongated.

Suture: Very smooth.

*Suture length.*—Approximately 3¾ inches, (95.25 mm.).

Stem cavity:

*Shape.*—Round.

*Stem cavity depth.*—Approximately ¼ inch (6.35 mm.).

Base: Flat.

Apex:

*Generally.*—Nearly flat.

*Apex shape.*—Slightly elongated and round.

Pistil point: Almost receded.

Ventral surface: Almost rounded.

Stem:

*Length.*—Approximately ½ inch, (12.7 mm.).

*Width.*—Approximately 1/16 inch (1.588 mm.).

Skin:

*Thickness.*—Approximately 1/64 inch (0.397 mm.) or less.

*Texture.*—Smooth.

*Tendency to crack.*—None observed.

*Color.*—Black (24 r. Black).

Flesh:

*Color.*—Deep Orange-yellow (69 deep O. y.).

*Texture of pit well.*—Slightly rough.

*Color of pit well.*—Dark Orange Yellow (72 d. oy.).

*Juice production.*—Medium juicy.

*Flavor.*—Mild, with no indication of tartness or acid taste; crisp.

*Aroma.*—Slight.

*Texture.*—Smooth and crisp.

*Fibers.*—None evident.

*Ripening.*—Even.

*Eating quality.*—Noteworthy.

Stone:

*Free or cling.*—Nearly full freestone.

*Fibers.*—None evident.

*Size.*—Length — approximately 1 inch, (25.4 mm.). Width — approximately ⅝ inch, (15.875 mm.). Thickness — approximately 3/8 inch, (9.525 mm.).

*Form.*—Elongated.

*Color.*—Yellowish-Brown (32 d. O.Y.).

*Base.*—Small and flat.

*Sides.*—Texture — nearly smooth.

*Ridges.*—None evident.

Use: Fresh market.

Keeping quality: Noteworthy; the subject variety has been tested in cold storage for periods up to and including three weeks, with no deleterious effects noted.

Shipping quality: Excellent; the subject variety stays firm and crisp for extended periods of time.

Although the new variety of plum tree possesses the desired characteristics under the growing conditions prevailing in Del Rey, Calif., in the central portion of the San Joaquin Valley, it is to be understood that variations of the usual magnitude in characteristics incident to changes in growing conditions, fertilization, pruning and pest control are to be expected.

Having described my new variety of plum tree, what I claim as new and desire to secure by Plant Letters Patent is:

1. A new and distinct variety of plum tree substantially as illustrated and described broadly characterized as to novelty by its maturity date which is approximately September 6 through September 10 under the ecological conditions prevailing at Del Rey, Calif., and by its producing fruit having a skin color that is Black, whose flesh is Deep Orange Yellow throughout and which has excellent handling and storage characteristics.

* * * * *

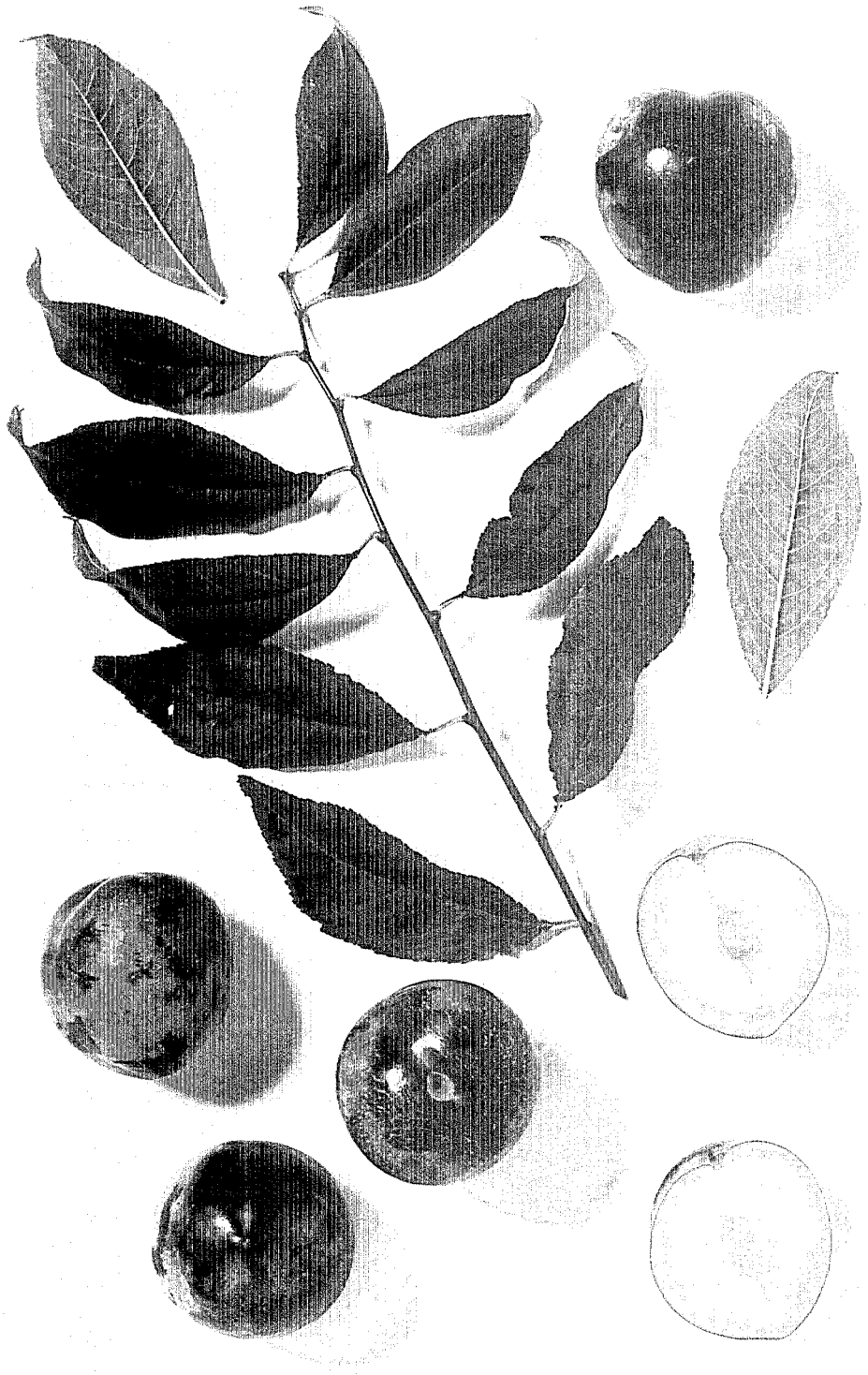

UNITED STATES PATENT AND TRADEMARK OFFICE

CERTIFICATE OF CORRECTION

PATENT NO. : PP 6,153

DATED : April 19, 1988

INVENTOR(S) : Thomas O. Chamberlin Sr.

It is certified that error appears in the above-identified patent and that said Letters Patent is hereby corrected as shown below:

Column 3, line 23, after "1 1/4" delete "1".

Signed and Sealed this

Twenty-third Day of August, 1988

*Attest:*

DONALD J. QUIGG

*Attesting Officer*

*Commissioner of Patents and Trademarks*